United States Patent
Bogan et al.

(10) Patent No.: US 6,849,433 B2
(45) Date of Patent: Feb. 1, 2005

(54) MICROBIAL PRODUCTION OF WAX ESTERS FROM HIGHLY BRANCHED ALKANES

(75) Inventors: William W. Bogan, Palatine, IL (US); Wendy R. Sullivan, Chicago, IL (US); James R. Paterek, Naperville, IL (US)

(73) Assignee: Gas Technology Institute, Des Plaines, IL (US)

( * ) Notice: Subject to any disclaimer, the term of this patent is extended or adjusted under 35 U.S.C. 154(b) by 7 days.

(21) Appl. No.: 10/354,135

(22) Filed: Jan. 29, 2003

(65) Prior Publication Data

US 2003/0235895 A1 Dec. 25, 2003

Related U.S. Application Data

(60) Provisional application No. 60/390,138, filed on Jun. 20, 2002.

(51) Int. Cl.[7] .............................. C12P 7/64; C12N 1/20; C12N 1/00
(52) U.S. Cl. ..................... 435/134; 435/252.1; 435/822
(58) Field of Search ............................. 435/134, 252.1, 435/822

(56) References Cited

U.S. PATENT DOCUMENTS

| | | |
|---|---|---|
| 3,409,506 A | 11/1968 | Stevens et al. |
| 4,404,283 A | 9/1983 | Neidleman et al. |
| 4,567,144 A | 1/1986 | Neidleman et al. |

FOREIGN PATENT DOCUMENTS

JP   55000065   *   5/1980

OTHER PUBLICATIONS

Lal et al. Journal of Applied Bacteriology. 1996, 81 (4), pp. 355–362.*

* cited by examiner

*Primary Examiner*—Vera Afremova
(74) *Attorney, Agent, or Firm*—Mark E. Fejer

(57) ABSTRACT

A microbial culture and method for producing wax esters using highly branched alkanes. In accordance with one embodiment, the highly branched alkane is squalane.

10 Claims, 1 Drawing Sheet

MICROBIAL PRODUCTION OF WAX ESTERS FROM HIGHLY BRANCHED ALKANES

CROSS REFERENCE TO RELATED APPLICATION

This application claims the benefit of an earlier filed provisional application having Serial No. 60/390,138 and a filing date of 20 Jun. 2002. +gi The U.S. Government has a paid-up license in this invention and the right in limited circumstances to require the patent owner to license others on reasonable terms as provided for by the terms of Contract No. DE-AC26-99BC15223 awarded by the U.S. Department of Energy.

BACKGROUND OF THE INVENTION

1. Field of the Invention

This invention relates to a method for producing wax esters biosynthetically. More particularly, this invention relates to a method for producing wax esters using highly branched alkanes as a starting material and a novel genus of soil bacteria, which appears to be closely related to *Acinetobacter*. The bacteria, designated as MVAB Hex1 (ATCC Accession Number PTA-4839) (ATCC, P.O. Box 1549, Manassas. Va. 20108), is exemplary of a suitable microorganism for producing wax esters in accordance with the method of this invention.

2. Description of Related Art

Wax esters are used in numerous industrial and commercial products, including cosmetics, candles and other wax-based products, inks, lubricants, and coatings. For example, long chain wax esters have been employed as a lubricant for providing mold release for molded products such as steel casting and for preventing destructive metal-to-metal contact under high temperature and/or pressure conditions, such as occur in a variety of industrial machines. Historically, the primary sources for such wax esters were natural sources such as the sperm whale and the jojoba plant. In recent years, certain microorganisms have been found to be suitable sources of wax esters. Through metabolic action, wax esters can be produced from inexpensive, readily available hydrocarbons. U.S. Pat. No. 3,409,506 to Stevens et al. teaches the biosynthesis of wax esters by aerobically subjecting aliphatic hydrocarbons to the metabolic action of a gram negative bacteria, *Micrococcus cerificans* (also referred to as *Acinetobacter* sp. HO1-N), in the presence of an aqueous mineral salts solution containing a limited concentration of mineral nutrients such as magnesium, calcium and combinations thereof. U.S. Pat. No. 4,404,283 to Neidleman et al. teaches a method for producing wax esters containing either 0,1 or 2 internally located carbon-carbon double bonds from saturated hydrocarbons, with no more than 1 carbon-carbon double bond being in fatty acid or the fatty alcohol segments by the metabolic action of microorganisms including *Mycobacterium ceriformans*, *Mycobacterium fortuitum*, *Mycobacterium rhodocrous*, *Candida lipolytica*, *Candida guilliermondii*, *Nocardia brasiliensis*, *Hormondendrum hordei*, *Rhizopus arrhizus*, *Fusarium lini*, *Corynebacterium paurometabolum*, *Corynebacterium diptheriae* and *Micrococcus cerificans*. Suitable starting materials are indicated to be $C_{15}$ through $C_{30}$ n-alkanes, n-alcohols and n-acids and petroleum hydrocarbon fractions in the $C_{15}$ through $C_{30}$ range. And, U.S. Pat. No. 4,567,144 to Neidleman et al. teaches a process for producing wax esters which includes aerobically incubating a culture of microorganisms of the genus *Acinetbacter* species HO1-N in an aqueous mineral salts solution containing ethanol as a primary food source.

It is axiomatic that the characteristics of products produced from wax esters are determined at least in part by the starting materials used to produce the wax esters. One characteristic of wax esters produced by known microbial systems is that the principal wax esters have a carbon chain length in the fatty acid and fatty alcohol segments equal to the chain length of the hydrocarbon used as the feedstock. Thus, the chain lengths of the fatty acid and fatty alcohol in the wax esters can be controlled by the chain length of the feedstock used. Likewise, microbial production of wax esters from aliphatic hydrocarbon chain feedstocks typically produces wax esters that are saturated rather than unsaturated. Such wax esters are not suitable for use as lubricant additives, which typically require that the wax esters have carbon chain lengths of at least 14 carbons in both the fatty acid and fatty alcohol segments and the presence of an internal carbon-carbon double bond in one or both segments. It will, thus, be apparent to those skilled in the art that the production of wax esters from more complex hydrocarbon feedstocks, such as highly branched alkane hydrocarbons, may result in a wider, more complex range of wax esters, which, in turn, provides the potential for improving existing products made from wax esters as well as the potential for developing new products.

Although chemical synthesis of wax esters is possible, microbial production of wax esters is preferable to chemical means of synthesis because it affords better control over the composition of the final product. The present invention deals with microbial processes for the production of wax esters, specifically using highly branched alkane hydrocarbons as a starting material.

SUMMARY OF THE INVENTION

It is one object of this invention to provide a method for producing wax esters from highly branched alkane hydrocarbons.

It is another object of this invention to provide a microbial culture suitable for producing wax esters from highly branched alkane hydrocarbons.

It is another object of this invention to enable the production of products including, but not limited to, cosmetics and personal-care products, inks and dyes, candles and other wax-based products, lubricants and coatings from wax esters produced from highly branched alkane hydrocarbons.

These and other objects of this invention are addressed by a method for producing wax esters comprising the steps of contacting a microbial culture suitable for producing wax esters using a highly branched alkane as a starting material under suitable conditions for producing said wax esters. In accordance with one embodiment of this invention, the microbial culture is MVAB Hex 1.

Heretofore, microbial cultures or strains capable of producing wax esters using highly branched alkane hydrocarbons as a starting material have not been known. The microbial strain disclosed and claimed herein is the first strain known to us that is capable of producing wax esters from the types of hydrocarbons (e.g. long-chain, highly-branched linear alkane hydrocarbons) which are covered in this application. It is possible that the wax esters formed from these starting hydrocarbons may have unique and/or unusual properties, relative to wax esters which are formed through microbial growth on more conventional hydrocarbon sources (e.g. short-chain, unbranched alkanes such as hexadecane). These properties, in turn, may confer upon these wax esters some utility in various industrial processes and products, such as those enumerated above.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

Figure 1A:
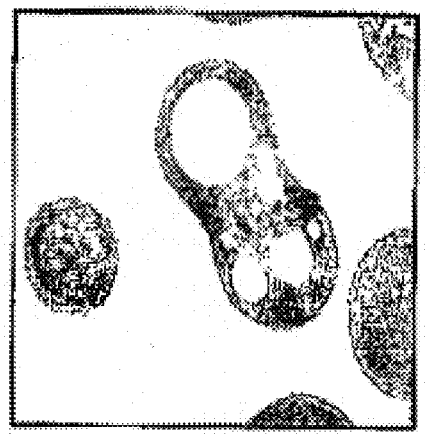
FIGS. 1A, 1B and 1C are images from a transmission electron microscope (TEM) examination of cells that show very significant amounts of wax esters produced in accordance with the method of this invention.

As used herein, the term "highly branched alkane" means an alkane hydrocarbon in which at least 20% of the main chain or backbone carbons are bonded to substituents. Preferred highly branched alkanes for use in this invention comprise in the range of about 20% to about 50% of the backbone carbons bonded to substituents. In accordance with one particularly preferred embodiment of this invention, a portion of the substituents are disposed proximate the terminal ends of the backbone carbon chain, creating ante-isoterminal branching.

As used herein, the term "substituent" means a hydrocarbon having in the range of 1–3 carbons. In accordance with one preferred embodiment of this invention, the preferred substituent is a hydrocarbon having one carbon, i.e. a methyl group.

Wax esters are formed in certain bacteria as a means of sequestering carbon-based material (as a future source of energy and of carbon for growth and biochemical processes) during periods of growth in which carbon is abundant relative to other nutrients; the most common limiting nutrient in such phases of "unbalanced" growth is nitrogen. In this way, wax esters can be thought of as the bacterial analogues of fat stored by higher animals. Chemically, wax esters consist of two hydrocarbon chains linked by an ester functional group in the following arrangement:

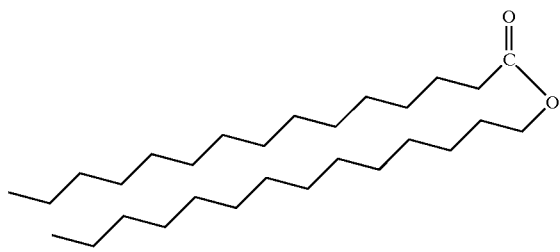

Depending upon the particular biochemical mechanisms employed by an individual strain, the hydrocarbon "tails" of wax ester molecules may consist of relatively unmodified hydrocarbon, or may be synthesized completely de novo from hydrocarbons which have been essentially completely catabolized (disassembled). In the former of these cases, the wax ester molecule retains many of the chemical characteristics of the starting hydrocarbon material.

We have isolated a bacterium from soils, obtained from an oil drilling field in Southern Illinois, which have been chronically contaminated by significantly high levels of crude oils (in the range of 10–15% petroleum hydrocarbon per dry weight of soil). This strain, which belongs to an apparently undescribed and novel genus which is related to *Acinetobacter*, is capable of optimal growth only in the presence of long-chain (typically $\geq C_{16}$) alkane hydrocarbons such as those present in crude oil. In addition to hexadecane, the strain, which we have designated MVAB Hex1, is capable of growth on heptadecane ($C_{17}H_{36}$), pristane (2,6,10,14-tetramethylpentadecane), and squalane (2,6,10,15,19,23-hexamethyltetracosane). The latter two of these are highly branched (methylated)alkane hydrocarbons, a class of compounds which was once thought to be almost entirely resistant to bacterial degradation and have in fact been used as markers or "bioindicators" in several studies of biodegradation of less-recalcitrant compounds. Although it has since been proven that several bacterial isolates are capable of biodegrading pristane, only two species, both belonging to the genus *Mycobacterium*, have been previously described as being able to biodegrade squalane. No strain or isolate of which we are aware has to date been described which displays wax ester production on either of these compounds, or on any closely-related (i.e. highly methylated or otherwise highly branched) hydrocarbon.

The site soil was reportedly contaminated with oil pumped from the Salem limestone formation (Mississippian Age), at a depth of approximately 3400 feet; contamination was very heavy, with TPH (total petroleum hydrocarbon) levels averaging 150,000 ppm (data not shown). Samples (ca. 4 grams) of soil were added to 50 ml of mineral salts medium (MSM), which was then further supplemented with 800 µl of either hexadecane or dodecane. After 3 days of shaking, the resultant enrichment cultures were then subcultured into fresh MSM (at the rate of 300 µl of primary culture to 50 ml medium), again supplemented with 800 µl of alkane. After one additional day of incubation, cultures were plated onto gelrite gellan gum plates, which were then overlaid with a layer of alkane (approximately 100 µl per plate) as a sole carbon source. Colonies were subcultured onto R2A agar (Difco), overlain with hexadecane, until pure (by visual inspection).

EXAMPLE 1

Figure 1B:
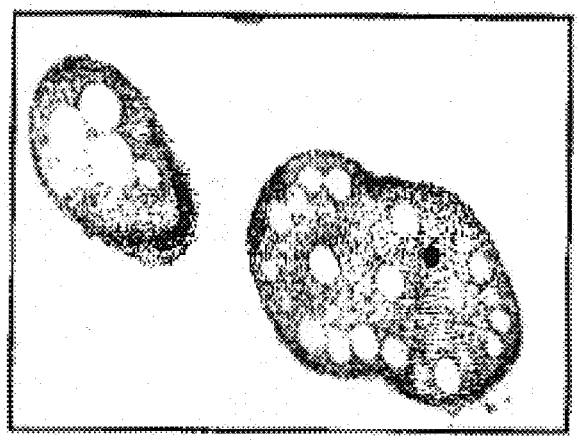
Figure 1C:
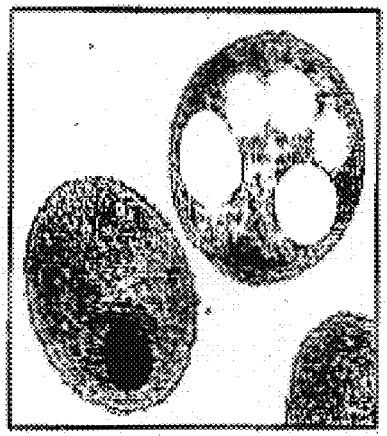

A bacterial strain designated MVAB Hex1 is cultured on a rich nutrient medium (such as R2A agar for solid-phase cultures, or LB broth for liquid cultures), or on minimal medium. Squalane (2,6,10,15,19,23-hexamethyltetracosane) is added to this medium, either as a separate liquid phase in liquid cultures, or as a liquid overlay which is spread over the solid medium (i.e. agar) prior to plating the bacteria. Within 24 to 48 hours, growth of MVAB Hex1 is clearly visible in (on) all of these media formulations. Collection of cells and examination by TEM (transmission electron microscopy) reveals the presence of significant quantities of wax ester inclusion bodies in the squalane-grown cells as shown in FIGS. 1A, 1B and 1C. These inclusion bodies are then collected (isolated) using various methods known to those skilled in the art based on gel permeation chromatography or density-gradient centrifugation.

EXAMPLE 2

MVAB Hex1, obtained from oil-contaminated site soils through the use of very short-term enrichment cultures in which hexadecane was added as a sole supplemental carbon source, grew poorly on R2A agar in the absence of hydrocarbon, producing small (~0.5 mm), translucent off-white colonies; in contrast, growth was much more vigorous in the presence of an overlayer of liquid hexadecane. In the latter case, colonies tended to be much larger, and frequently showed convergent growth along the path of the streak used to inoculate the plate. When the isolate was subcultured from hexadecane-overlain plates to hydrocarbon-less R2A plates, growth remained vigorous for 1–2 successive transfers, then began to decrease, eventually reaching the same poor level of growth seen when cultured directly to these plates.

EXAMPLE 3

MVAB Hex1 was cultured on agar plates. In the absence of supplementation (in the form of a liquid overlayer) with alkane hydrocarbon, growth was very poor under these conditions, even on fairly rich nutrient media (such as R2A or MacConkey agars or LB broth). When alkane hydrocarbon was provided, however, growth of the strain became much more vigorous. Transmission electron microscopic (TEM) examination of cells thus cultured showed that, in the presence of certain alkane hydrocarbons, very significant amounts of wax ester were produced, in the form of localized "inclusion bodies", similar to those which have been microscopically visualized in other bacteria. Although these inclusion bodies tended to be most prevalent during growth of cells on agar plates which were overlain with hexadecane, they were also frequently observed in cells grown on squalane. Squalane-derived inclusion bodies were frequently observed to take up a significant amount of the total intracellular volume, as in the cases shown in FIGS. 1A, 1B and 1C.

As described above, the fact of the MVAB Hex1 isolate to grow on squalane at all is an unexpected result, given that only two bacterial strains, both members of the genus *Mycobacterium* have ever been described as being able to grow on this compound, due to its high molecular weight, high degree of branching (including terminal substitutions which inhibit the β-oxidation pathway for alkane metabolism) and high hydrophobicity. No strain has ever been shown to produce wax esters derived from squalane or any related hydrocarbon; thus, this result was very unexpected.

As described above, we have discovered at least one strain, MVAB Hex1, that is capable of wax ester production during growth on highly branched, heavily methylated compounds such as squalane. Thus, if the wax esters thereby produced are found to display or possess unique or useful chemical properties, use of this strain (or of ones which are genetically and biochemically related to it) will be the only available method for the microbial production of wax esters from this type of starting material.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. An isolated microbial culture comprising strain MVAB Hex 1 (ATCC PTA 4839) which produces at least one wax ester when contacted with at least one highly branched alkane.

2. The isolated microbial culture in accordance with claim 1, wherein said at least one highly branched alkane is a methylated alkane.

3. The isolated microbial culture in accordance with claim 1, wherein said at least one highly branched alkane is squalane.

4. The isolated microbial culture in accordance with claim 1, wherein said at least one highly branched alkane is pristane.

5. The isolated microbial culture in accordance with claim 1, wherein at least one highly branched alkane comprises at least 16 carbons.

6. A method for producing wax esters comprising the steps of:

contacting with a highly branched alkane a microbial culture suitable for producing wax esters using said highly branched alkane under suitable conditions for producing said wax esters, forming at least one said wax ester wherein the microbial culture is strain MVAX Hex 1 (ATCC PTA 4839).

7. A method in accordance with claim 6, wherein said highly branched alkane comprises at least 16 carbons.

8. A method in accordance with claim 6, wherein said highly branched alkane is a methylated alkane.

9. A method in accordance with claim 6, wherein said highly branched alkane is squalane.

10. A method in accordance with claim 6, wherein said highly branched alkane is pristane.

* * * * *